United States Patent
Umeuchi et al.

(10) Patent No.: US 9,051,335 B2
(45) Date of Patent: Jun. 9, 2015

(54) ANTIPRURITIC AGENT FOR PRURITUS CAUSED BY MULTIPLE SCLEROSIS

(75) Inventors: Hideo Umeuchi, Kamakura (JP); Koki Ueno, Tokyo (JP); Hiroshi Miyakawa, Kawasaki (JP)

(73) Assignee: TORAY INDUSTRIES, INC., Tokyo (JP)

( * ) Notice: Subject to any disclaimer, the term of this patent is extended or adjusted under 35 U.S.C. 154(b) by 989 days.

(21) Appl. No.: 11/885,946

(22) PCT Filed: Mar. 9, 2006

(86) PCT No.: PCT/JP2006/304655
§ 371 (c)(1),
(2), (4) Date: May 22, 2008

(87) PCT Pub. No.: WO2006/095836
PCT Pub. Date: Sep. 14, 2006

(65) Prior Publication Data
US 2009/0170888 A1 Jul. 2, 2009

(30) Foreign Application Priority Data

Mar. 10, 2005 (JP) .................................. 2005-066666

(51) Int. Cl.
*A61K 31/439* (2006.01)
*C07D 489/06* (2006.01)
*A61P 25/28* (2006.01)
*C07D 491/10* (2006.01)
*A61K 31/485* (2006.01)

(52) U.S. Cl.
CPC ............ *C07D 491/10* (2013.01); *A61K 31/485* (2013.01)

(58) Field of Classification Search
USPC .................................................. 514/255.05
See application file for complete search history.

(56) References Cited

U.S. PATENT DOCUMENTS

| | | | | |
|---|---|---|---|---|
| 5,401,770 A | * | 3/1995 | Taguchi et al. | 514/494 |
| 6,174,891 B1 | * | 1/2001 | Nagase et al. | 514/282 |
| 2005/0197341 A1 | * | 9/2005 | Woolf et al. | 514/251 |

FOREIGN PATENT DOCUMENTS

| EP | 1 310 251 | 5/2003 |
|---|---|---|
| JP | 2001-163784 A | 6/2001 |

(Continued)

OTHER PUBLICATIONS

Yamamoto et al. (Paroxysmal itching in multiple sclerosis: a report of three cases, Journal of Neurology, Neurosurgery, and Psychiatry, 1981, 44,19-22.*

(Continued)

*Primary Examiner* — San-Ming Hui
*Assistant Examiner* — Andrew Lee
(74) *Attorney, Agent, or Firm* — Birch, Stewart, Kolasch & Birch, LLP

(57) ABSTRACT

An antipruritic against pruritus caused by multiple sclerosis is disclosed. The antipruritic comprises as an effective ingredient an κ opioid receptor agonist compound having a 4,5-epoxymorphinan skeleton and having a specific chemical structure, such as Compound 1 having the following structure:

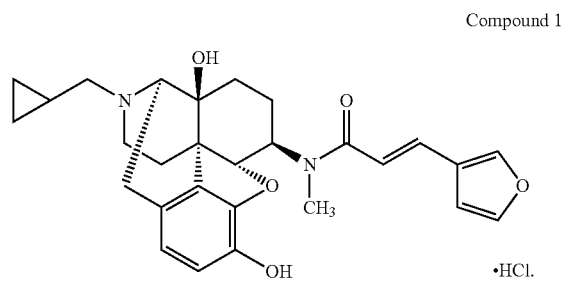

11 Claims, 2 Drawing Sheets

(56) References Cited

FOREIGN PATENT DOCUMENTS

| | | |
|---|---|---|
| JP | 2002-308769 A | 10/2002 |
| WO | WO-01/14383 A1 | 3/2001 |
| WO | WO 01/41705 | 6/2001 |

OTHER PUBLICATIONS

Twycross et al. (Itch: scratching more than the surface ,QJM 92003) 96 (1): 7-26, pp. 1-29.*

* cited by examiner

ANTIPRURITIC AGENT FOR PRURITUS CAUSED BY MULTIPLE SCLEROSIS

TECHNICAL FIELD

The present invention relates to an antipruritic against pruritus caused by multiple sclerosis.

BACKGROUND ART

Multiple sclerosis (MS) is one of the inflammatory demyelinating diseases of central nervous system and is characterized by multiple occurrence in terms of time and space. In Japan, there are about 10,000 patients suffering from the disease, and thus the disease is a rare disease and is designated as an intractable disease. Japan Intractable Diseases Information Center administered cooperatively by Ministry of Health, Labour and Welfare, Health Service Bureau, Diseases Control Division and Japan Intractable Diseases Research Foundation defines multiple sclerosis as follows:

The cause of multiple sclerosis has not been clarified. In general, infiltration of lymphocytes and macrophages into nerve tissue is observed, and from the blood biochemical viewpoint, drastic increase in blood IgG with respect to the total proteins is observed, so that the disease is thought to be caused by inflammation mechanism. However, since a specific pathogen such as a virus is not found in the site of inflammation, it has been suggested that autoimmune mechanism is involved in the formation of lesions. Although myelin basic protein (MBP) level raises in some cases reflecting the collapse of myelin, it is not specific to multiple sclerosis. The symptoms of multiple sclerosis differ depending on the damaged site in the nervous system, and visual disorders, diplopia, cerebellar ataxia, quadriplegia, sensory disturbances and the like are observed (for example, Non-patent Literature 1).

One of the sensory disturbances is severe pruritus (itching), and the pruritus emerges in cases where the dorsal horn of the spinal cord is damaged (for example, Non-patent Literature 2). The pruritus is characterized by the fact that pruritus lasting several minutes occurs spasmodically several times a day. The favorite sites of the pruritus are relatively bilateral in accordance with the segments of innervation by cervical and thoracic nerves. The feeling of the pruritus is unbearable itching like that felt after insect bite by a small insect. If the pruritus occurs in night, sleep is disturbed (for example, Non-patent Literature 3). Although no eruption is observed on the skin, the skin sometimes has erosions due to vigorous scratching. In most cases, the pruritus is observed at the initial stage in the advanced stage. Although the generated pruritus is reduced once, it lasts many years. There are cases where the pruritus is induced by a touch on the skin. Antihistamines have almost no effects against the pruritus. Since it has been confirmed that some of the drugs which inhibit neuronal firing, such as carbamazepine, phenyloin and mexiletine are partly effective for the pruritus, it has been suggested that the pruritus accompanied by multiple sclerosis is different from ordinary pruritus. Although it has been reported that steroid pulse therapy in which a large amount of a steroid is administered by drip infusion for 3 to 5 days is effective (for example, Non-patent Literature 4), the therapy requires hospitalization for treatment, and many side effects caused by the systemic administration of the steroid, such as infections, digestive ulcers, obesity, diabetes, osteoporosis and mood disorder, are problematic (Non-patent Literature 5). Dermatologists express the pruritus as a strange symptom, which pruritus cannot be stopped by scratching and which may lead to a damage of skin by scratching, that can be called a self-injurious behavior (for example, Non-patent Literature 2).

In spite of the fact that the pruritus caused by multiple sclerosis is very uncomfortable and is a symptom which reduces quality of life, the mechanism is unclear and effective therapeutic method has not been established, which is a big problem in medicine. Development of a more effective therapeutic drug is strongly demanded.

In recent years, it has been suggested that agonist compounds for the κ opioid receptor which is one of the opioid receptors have antipruritic activities (for example, Non-patent Literature 6). It has been reported that κ opioid receptor agonist compounds having 4,5-epoxymorphinan skeleton may be used as an antipruritic for general pruritises accompanied by, for example, dermatoses such as atopic dermatitis, neurodermatitis, contact dermatitis, seborrheic dermatitis, autosensitization dermatitis, caterpillar dermatitis, asteatosis, senile pruritus cutaneous, insect sting, photosensitive dermatitis, urticaria, prurigo, herpes, impetigo, eczema, tinea, lichen, psoriasis, scabies and acne vulgaris; and visceral diseases such as malignant tumors, diabetes mellitus, hepatic diseases, renal failure, renal dialysis and pregnancy (for example, see Patent Literature 1).

However, whether or not the κ opioid receptor agonist compounds are effective for pruritus caused by multiple sclerosis was unknown, which is a neurological disorder and not a dermatosis or internal disease, the characteristics and therapies for the pruritus being largely different from normal pruritus.

Patent Literature 1: Japanese Patent Publication No. 3531170
Non-patent Literature 1: Neuromuscular Disorders Research Group (immunologic nuerological diseases) "Guidelines for Diagnosis and Therapy>multiple sclerosis" [online] Jun. 20, 2005, Japan Intractable Diseases Information Center, [searched on Feb. 27, 2006], internet <http://www.nan-byou.or.jp/sikkan/068_i.htm>
Non-patent Literature 2: Kiyoharu INOUE, "Sogo Rinsho" (Japan), 2004, Vol. 53, No. 5, p. 1807-1811
Non-patent Literature 3: Yoshiki MIYAJI eds., "Pruritus Q & A", (Japan), First Edition, Iyaku (Medicine and Drug) Journal Co., Ltd., 1997, p. 86-87
Non-patent Literature 4: Kiyoharu INOUE, "Japan Medical Journal" (Japan), 2003, Vol. 4157, p. 85
Non-patent Literature 5: Takashi YAMAMURA (editor, National Center of Neurology and Psychiatry, National Institute of Neuroscience), "Outlines of Multiple Sclerosis", [online], March, 2004, Specified Nonprofit Corporation MS CABIN, searched on Feb. 27, 2006, internet <http://www.mscabin.org/ms08.html>
Non-patent Literature 6: European Journal of Pharmacology, (Netherlands), 2002, Vol. 435, No. 2-3, p. 259-264

DISCLOSURE OF THE INVENTION

Problems which the Invention Tries to Solve

Since the characteristics of the pruritus caused by multiple sclerosis which is a neurological disorder are different from those of normal pruritus, the existing antipruritics are not effective in most cases. Thus, there is a problem that QOL of the patients is very poor.

An object of the present invention is to provide an antipruritic for the pruritus caused by multiple sclerosis, which does not exist in the prior art.

Means for Solving the Problem

The present inventors intensively studied for developing an antipruritic against pruritus caused by multiple sclerosis in order to solve the above-described problem. As a result, the present inventors discovered that κ opioid receptor agonist compounds having 4,5-epoxymorphinan skeleton have an activity to inhibit scratching behavior of MRL/lpr mice which are widely used as models for autoimmune diseases, so that they are particularly useful as antipruritics against pruritus caused by multiple sclerosis, thereby completing the present invention. That is, the present invention provides an antipruritic against pruritus caused by multiple sclerosis, comprising as an effective ingredient a compound of the following Formula (I):

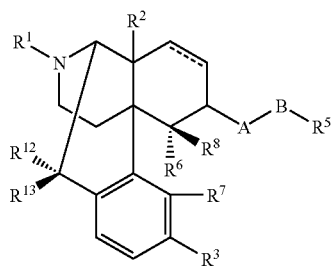

(I)

[wherein ⋯ represents a double bond or single bond;

$R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (wherein the number of carbon atoms in the alkyl moiety is 1 to 5) or thiophen-2-ylalkyl (wherein the number of carbon atoms in the alkyl moiety is 1 to 5);

$R^2$ represents hydrogen, hydroxy, nitro, $C_1$-$C_5$ alkanoyloxy, $C_1$-$C_5$ alkoxy, $C_1$-$C_5$ alkyl or $NR^9R^{10}$ wherein $R^9$ represents hydrogen or $C_1$-$C_5$ alkyl and $R^{10}$ represents hydrogen or $C_1$-$C_5$ alkyl or —C(=O)$R^{11}$ wherein $R^{11}$ represents hydrogen, phenyl or $C_1$-$C_5$ alkyl;

$R^3$ represents hydrogen, hydroxy, $C_1$-$C_5$ alkanoyloxy or $C_1$-$C_5$ alkoxy;

A represents —XC(=Y)—, —XC(=Y)Z—, —X— or —XSO$_2$— (wherein X, Y and Z independently represent $NR^4$, S or O wherein $R^4$ represents hydrogen, $C_1$-$C_5$ linear or branched alkyl or $C_6$-$C_{12}$ aryl, and wherein $R^4$s in the formula may be the same or different);

B represents valence bond, $C_1$-$C_{14}$ linear or branched alkylene (wherein the alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), $C_2$-$C_{14}$ linear or branched acyclic unsaturated hydrocarbon containing 1 to 3 double bonds and/or triple bonds (wherein the acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), or $C_1$-$C_{14}$ linear or branched saturated or unsaturated hydrocarbon containing 1 to 5 thioether bonds, ether bonds and/or amino bonds (with the proviso that a hetero atom does not directly binds to A, and wherein 1 to 3 methylene groups therein may be replaced by a carbonyl group(s));

$R^5$ represents hydrogen or an organic group having a skeleton selected from those shown below

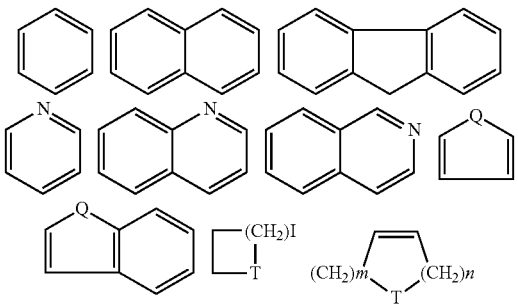

Q: N, O, S
T: CH, N, S, O
l = 0-5
m, n ≧ 0
m + n ≦ 5

Organic Groups Represented by $R^5$ (wherein Q represents N, O or S; T represents CH$_2$, NH, S or O; l represents an integer of 0 to 5; and m and n independently represent integers of 0 to 5, the total of m and n being not more than 5; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy);

$R^6$ represents hydrogen; $R^7$ represents hydrogen, hydroxy, $C_1$-$C_5$ alkoxy or $C_1$-$C_5$ alkanoyloxy; or $R^6$ and $R^7$ together represent —O—, —CH$_2$— or —S—;

$R^8$ represents hydrogen, $C_1$-$C_5$ alkyl or $C_1$-$C_5$ alkanoyl; and $R^{12}$ and $R^{13}$ both represent hydrogen, or one of them represents hydrogen and the other represents hydroxy, or they together represent oxo; and the Formula (I) includes (+), (−) and (±) isomers]

or a pharmaceutically acceptable acid addition salt thereof. The present invention also provides a use of the compound represented by the above-described Formula (I) or the pharmaceutically acceptable acid addition salt thereof for the production of an antipruritic. The present invention further provides a method for preventing or reducing pruritus caused by multiple sclerosis, comprising administering an effective amount of the compound represented by the above-described Formula (I) or the pharmaceutically acceptable acid addition salt thereof to a patient suffering from multiple sclerosis.

Effects of the Invention

By the present invention, a therapeutic drug for pruritus caused by multiple sclerosis for which effective therapy was hitherto not present was provided. The antipruritic according to the present invention has an excellent reducing effect against the pruritus caused by multiple sclerosis. Therefore, by administering the antipruritic according to the present invention to a patient suffering from multiple sclerosis, the pruritus of the patient is reduced, and the quality of life of the patient is improved.

BRIEF DESCRIPTION OF THE DRAWINGS

FIG. 1-2 shows the relationship between the age in week and serum IgG antibody level or serum IgE antibody level in male MRL/lpr mice used in Example of the present invention.

FIG. 2 shows the relationship between the dose of Compound 1 of the present invention and the number of scratching behavior, and the relationship between the dose of chlorophenylamine which is an antihistaminic agent and the number of scratching behavior, which relationships were determined in the Example of the present invention.

BEST MODE FOR CARRYING OUT THE INVENTION

Figure 1:
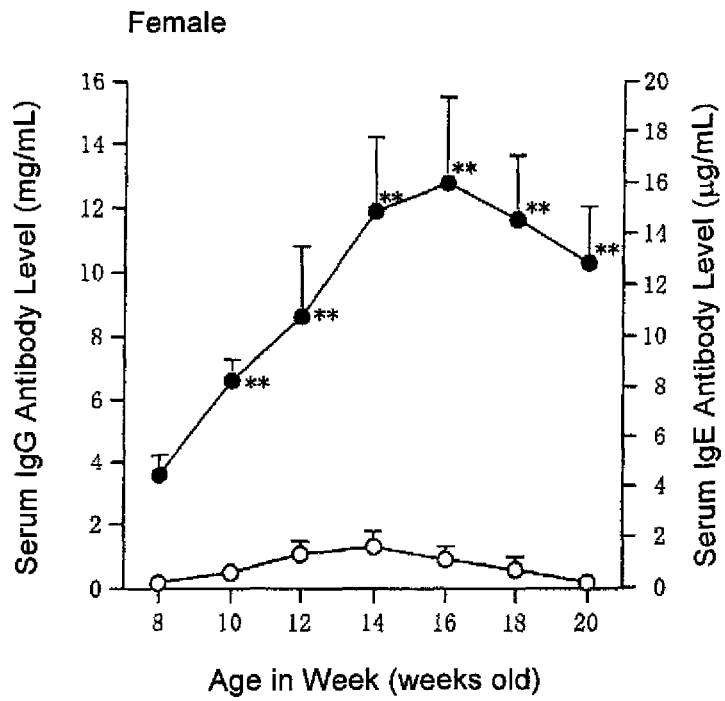
FIG. 1-1 shows the relationship between the age in week and serum IgG antibody level or serum IgE antibody level in female MRL/lpr mice used in Example of the present invention.

As described above, the antipruritic according to the present invention comprises as an effective ingredient a compound represented by the above-described Formula (I) or a pharmaceutically acceptable acid addition salt thereof.

In Formula (I), as the $R^1$, $C_1$-$C_5$ alkyl, $C_4$-$C_7$ cycloalkylmethyl, $C_5$-$C_7$ cycloalkenylmethyl, $C_7$-$C_{13}$ phenylalkyl, $C_4$-$C_7$ alkenyl, allyl, furan-2-yl-alkyl (wherein the number of carbon atoms in the alkyl moiety is 1 to 5) or thiophen-2-yl-alkyl (wherein the number of carbon atoms in the alkyl moiety is 1 to 5) is preferred, and methyl, ethyl, propyl, butyl, isobutyl, cyclopropylmethyl, allyl, benzyl or phenethyl is especially preferred.

As the $R^2$, hydrogen, hydroxy, nitro, acetoxy, methoxy, methyl, ethyl, propyl, amino, dimethylamino, acetyl amino or benzoylamino is preferred, and hydrogen, hydroxy, nitro, acetoxy, methoxy, methyl, dimethylamino, hydrogen, hydroxy, acetoxy or methoxy is especially preferred.

As the $R^3$, hydrogen, hydroxy, acetoxy or methoxy is preferred, and hydroxy, acetoxy or methoxy is especially preferred.

As the "A", —XC(=Y)— (wherein X represents $NR^4$, S or O, Y represents O, wherein $R^4$ represents hydrogen or $C_1$-$C_5$ linear or branched alkyl), —XC(=Y)Z—, —X— or —$XSO_2$— (wherein X represents $NR^4$, Y represents O or S, and Z represents $NR^4$ or O, wherein $R^4$ represents hydrogen or $C_1$-$C_5$ linear or branched alkyl) is preferred, and —XC(=Y)— or —XC(=Y)Z— (wherein X represents $NR^4$, Y represents O, and Z represents O, wherein $R^4$ represents $C_1$-$C_5$ linear or branched alkyl) is more preferred, and —XC(=Y)— (wherein X represents $NR^4$, and Y represents O, wherein $R^4$ represents $C_1$-$C_5$ linear or branched alkyl) is especially preferred. More specifically, —$NR^4$C(=O)—, —SC(=O)—, —OC(=O)—, —$NR^4$C(=O)$NR^4$—$NR^4$C(=S)$NR^4$—, —$NR^4$C(=O)O—, —$NR^4$C(=S)O—, —$NR^4$— or —$NR^4SO_2$— is preferred, —$NR^4$C(=O)— or —$NR^4$C(=O)O— is more preferred, and —$NR^4$C(=O)— is especially preferred.

As the $R^4$, hydrogen or $C_1$-$C_5$ linear or branched alkyl is preferred, and $C_1$-$C_5$ linear or branched alkyl, especially methyl, ethyl, propyl, butyl or isobutyl is preferred.

As the "B", —$(CH_2)_n$— (n=0-10), —$(CH_2)_n$—C(=O)— (n=1-4), —CH=CH—$(CH_2)_n$—(n=0-4), —C≡C—$(CH_2)_n$— (n=0-4), —$CH_2$—O—, —$CH_2$—S—, —$(CH_2)_2$—O—$CH_2$— or —CH=CH—CH=CH—$(CH_2)_n$— (n=0-4) is preferred, —$(CH_2)_n$— (n=1-3), —CH=CH—$(CH_2)_n$— (n=0-4), —C≡C—$(CH_2)_n$— (n=0-4), —$CH_2$—O— or —$CH_2$—S— is more preferred, $C_1$-$C_3$ linear alkylene, —CH=CH—, —C≡C—, —$CH_2$O— or —$CH_2$S— is especially preferred, and among these, —CH=CH— or —C≡C— is preferred (of course, these preferred examples include those having the substitutions with the above-described various substituents, or replacements).

As the $R^5$, hydrogen or an organic group having a skeleton selected from those shown below

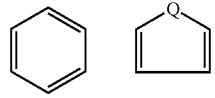

Q: O,S

Organic Groups Represented by $R^5$
(wherein Q represents O or S; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy) is preferred. Among these, hydrogen, phenyl, thienyl, furanyl (each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy) is especially preferred.

Specific preferred examples include, but not limited to, hydrogen, phenyl, 2-methylphenyl, 3-methylphenyl, 4-methylphenyl, 3,4-dimethylphenyl, 3,5-dimethylphenyl, 2-methoxyphenyl, 3-methoxyphenyl, 4-methoxyphenyl, 3,4-dimethoxyphenyl, 3-hydroxyphenyl, 4-hydroxyphenyl, 3,4-dihydroxyphenyl, 2-fluorophenyl, 3-fluorophenyl, 4-fluorophenyl, 3,4-difluorophenyl, perfluorophenyl, 2-chlorophenyl, 3-chlorophenyl, 4-chlorophenyl, 2,4-dichlorophenyl, 3,4-dichlorophenyl, 2,4,5-trichlorophenyl, 2,4,6-trichlorophenyl, 2-bromophenyl, 3-bromophenyl, 4-bromophenyl, 2-nitrophenyl, 3-nitrophenyl, 4-nitrophenyl, 2-aminophenyl, 3-aminophenyl, 4-aminophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 3,4-methylenedioxyphenyl, 2-furanyl, 3-furanyl, 2-thienyl and 3-thienyl.

As the $R^6$ and $R^{27}$, those together form —O—, —$CH_2$— or —S— are preferred, and those together form —O— are especially preferred.

As the $R^8$, hydrogen, $C_1$-$C_5$ alkyl or $C_1$-$C_5$ alkanoyl is preferred, hydrogen, methyl, ethyl or propyl is more preferred, and hydrogen is especially preferred.

As for the $R^{12}$ and $R^{13}$, those wherein both represent hydrogen, or one of them represent hydroxy, or they together represent oxo are preferred, and those wherein both of them are hydrogen, or one of them represent hydroxy are more preferred, and those wherein both of them are hydrogen is especially preferred.

Further, the antipruritics against pruritus caused by multiple sclerosis, comprising as an effective ingredient a compound represented by the above-described Formula (I), wherein $R^1$ is methyl, ethyl, propyl, butyl, isobutyl, cyclopropylmethyl, allyl, benzyl or phenethyl; $R^2$ and $R^3$ independently are hydrogen, hydroxy, acetoxy or methoxy; A is —XC(=Y)— (wherein X represents $NR^4$, S or O, and Y represents O, wherein $R^4$ represents $C_1$-$C_5$ linear or branched alkyl)-XC(=Y)Z—, —X— or —$XSO_2$— (wherein X represents $NR^4$, Y represents O or S, and Z represents $NR^4$ or O, wherein $R^4$ represents hydrogen or $C_1$-$C_5$ linear or branched alkyl); B is $C_1$-$C_3$ linear alkylene; $R^6$ and $R^7$ together form —O—; and $R^8$ is hydrogen; or a pharmaceutically acceptable acid addition salt thereof are preferred. Among these, the antipruritics against pruritus caused by multiple sclerosis, comprising as an effective ingredient a compound represented by the Formula (I), wherein A is —XC(=Y)— or —XC(=Y)Z— (wherein X represents $NR^4$, Y represents O, and Z represents O, wherein $R^4$ represents $C_1$-$C_5$ linear or branched alkyl); or a pharmaceutically acceptable acid addition salt thereof are preferred. Further, the antipruritics against pruritus caused by multiple sclerosis, comprising as an effective ingredient a compound represented by the above-described Formula (I), wherein $R^5$ is hydrogen or an organic group having a skeleton selected from those shown below

Q: O,S

Organic Groups Represented by $R^5$
(wherein Q represents O or S; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy);
or a pharmaceutically acceptable acid addition salt thereof are preferred. Among the latter, the antipruritics against pruritus caused by multiple sclerosis, comprising as an effective ingredient a compound represented by the above-described Formula (I), wherein A is —XC(=Y)— or —XC(=Y)Z— (wherein X represents $NR^4$, Y represents O, and Z represents O, wherein $R^4$ represents $C_1$-$C_5$ linear or branched alkyl) or a pharmaceutically acceptable acid addition salt thereof are preferred.

Further, the antipruritics against pruritus caused by multiple sclerosis, comprising as an effective ingredient a compound represented by the above-described Formula (I), wherein $R^1$ is methyl, ethyl, propyl, butyl, isobutyl, cyclopropylmethyl, allyl, benzyl or phenethyl; $R^2$ and $R^3$ independently are hydrogen, hydroxy, acetoxy or methoxy; A is —XC(=Y)— (wherein X represents $NR^4$, and Y represents O, wherein $R^4$ represents $C_1$-$C_5$ linear or branched alkyl); B is —CH=CH—, —C≡C—, —$CH_2$O— or —$CH_2$S—; $R^6$ and $R^7$ together form —O—; and $R^8$ is hydrogen; or a pharmaceutically acceptable acid addition salt thereof are preferred. Among these, the antipruritics against pruritus caused by multiple sclerosis, comprising as an effective ingredient a compound of Formula (I) wherein $R^5$ is hydrogen or an organic group having a skeleton selected from those shown below

Q: O,S

Organic Groups Represented by $R^5$
(wherein Q represents O or S; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy);
or a pharmaceutically acceptable acid addition salt thereof, as well as those comprising as an effective ingredient a compound of Formula (I) wherein B is —CH=CH— or —C≡C—, or a pharmaceutically acceptable acid addition salt thereof, are preferred. Among the latter, the antipruritics against pruritus caused by multiple sclerosis, comprising as an effective ingredient a compound of Formula (I) wherein $R^5$ is hydrogen or an organic group having a skeleton selected from those shown below

Q: O,S

Organic Groups Represented by $R^5$
(wherein Q represents O or S; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy) or a pharmaceutically acceptable acid addition salt thereof, are preferred.

Specific examples of the compounds represented by Formula (I) are listed below, but the compounds are not limited thereto.
17-cyclopropylmethyl-4,5α-epoxy-3,14β-dihydroxy-6α-(N-methylphenylacetamido)morphinan, 17-cyclopropylmethyl-4,5α-epoxy-3,14β-dihydroxy-6β-(N-methylphenylacetamido)morphinan, 17-cyclopropylmethyl-4,5α-epoxy-3,14β-dihydroxy-6α-(N-methyl-3-fluorophenylacetamido)morphinan,
17-cyclopropylmethyl-4,5α-epoxy-3,14β-dihydroxy-6β-(N-methyl-3-fluorophenylacetamido)morphinan, 17-cyclopropylmethyl-4,5α-epoxy-3,14β-dihydroxy-6α-(N-methyl-3,4-difluorophenylacetamido)morphinan,
17-cyclopropylmethyl-4,5α-epoxy-3,14β-dihydroxy-6β-(N-methyl-3,4-difluorophenylacetamido)morphinan, 17-cyclopropylmethyl-4,5α-epoxy-3,14β-dihydroxy-6α-(N-methyl-3-chlorophenylacetamido)morphinan, 17-cyclopropylmethyl-4,5α-epoxy-3,14β-dihydroxy-6β-(N-methyl-3-chlorophenylacetamido)morphinan,
17-cyclopropylmethyl-4,5α-epoxy-3,14β-dihydroxy-6α-(N-methyl-4-chlorophenylacetamido)morphinan, 17-cyclopropylmethyl-4,5α-epoxy-3,14β-dihydroxy-6β-(N-methyl-4-chlorophenylacetamido)morphinan,
17-cyclopropylmethyl-4,5α-epoxy-3,14β-dihydroxy-6α-(N-methyl-3,4-dichlorophenylacetamido)morphinan, 17-cyclopropylmethyl-4,5α-epoxy-3,14β-dihydroxy-6β-(N-methyl-3,4-dichlorophenylacetamido)morphinan,
17-cyclopropylmethyl-4,5α-epoxy-3,14β-dihydroxy-6α-(N-methyl-3-bromophenylacetamido)morphinan, 17-cyclopropylmethyl-4,5α-epoxy-3,14β-dihydroxy-6β-(N-methyl-3-bromophenylacetamido)morphinan,
17-cyclopropylmethyl-4,5α-epoxy-3,14β-dihydroxy-6α-(N-methyl-4-bromophenylacetamido)morphinan, 17-cyclopropylmethyl-4,5α-epoxy-3,14β-dihydroxy-6β-(N-methyl-4-bromophenylacetamido)morphinan,
17-cyclopropylmethyl-4,5α-epoxy-3,14β-dihydroxy-6α-(N-methyl-3-trifluoromethylphenylacetamido)morphinan, 17-cyclopropylmethyl-4,5α-epoxy-3,14β-dihydroxy-6β-(N-methyl-3-trifluoromethylphenylacetamido)morphinan, 17-cyclopropylmethyl-4,5α-epoxy-3,14β-dihydroxy-6α-(N-methyl-4- trifluoromethylphenylacetamido)morphinan, 17-cyclopropylmethyl-4,5α-epoxy-3,14β-dihydroxy-6β-(N-methyl-4-trifluoromethylphenylacetamido)morphinan, 17-cyclopropylmethyl-4,5α-epoxy-3,14β-dihydroxy-6α-(N-methyl-3-nitrophenylacetamido) morphinan, 17-cyclopropylmethyl-4,5α-epoxy-3,14β-dihydroxy-6β-(N-methyl-3-nitrophenylacetamido) morphinan, 17-cyclopropylmethyl-4,5α-epoxy-3,14β-dihydroxy-6α-(N-methyl-cinnamamido)morphinan, 17-cyclopropylmethyl-4,5α-epoxy-3,14β-dihydroxy-6β-(N-methyl-cinnamamido)morphinan, 17-cyclopropylmethyl-4,5α-epoxy-3,14β-dihydroxy-6α-(N-methyl-3-fluorocinnamamido)morphinan, 17-cyclopropylmethyl-4,5α-epoxy-3,14β-dihydroxy-6β-(N-methyl-3-fluorocinnamamido)morphinan, 7-cyclopropylmethyl-4,5α-epoxy-3,14β-dihydroxy-6α-(N-methyl-4-fluorocinnamamido)morphinan, cyclopropylmethyl-4,5α-epoxy-3,14β-dihydroxy-6β-(N-methyl-4-fluorocinnamamido)morphinan, 17-cyclopropylmethyl-4,5α-epoxy-3,14β-dihydroxy-6α-(N-methyl-3,4-difluorocinnamamido)morphinan, 17-cyclopropylmethyl-4,5α-epoxy-3,14β-dihydroxy-6β-(N-methyl-3,4-difluorocinnamamido)morphinan, 17-cyclopropylmethyl-4,5α-epoxy-3,14β-dihydroxy-6α-(N-methyl-3-chlorocinnamamido)morphinan, 17-cyclopropylmethyl-4,5α-epoxy-3,14β-dihydroxy-6β-(N-methyl-3-chlorocinnamamido)morphinan, 17-cyclopropylmethyl-4,5α-epoxy-3,14β-dihydroxy-6α-(N-methyl-4-chlorocinnamamido)morphinan, 17-cyclopropylmethyl-4,5α-epoxy-3,14β-dihydroxy-6β-(N-methyl-4-chlorocinnamamido)morphinan, 17-cyclopropylmethyl-4,5α-epoxy-3,14β-dihydroxy-6α-(N-methyl-3,4-dichlorocinnamamido)morphinan, 17-cyclopropylmethyl-4,5α-epoxy-3,14β-dihydroxy-6β-(N-methyl-3,4-dichlorocinnamamido)morphinan, 17-cyclopropylmethyl-4,5α-epoxy-3,14β-dihydroxy-6α-(N-methyl-3-bromocinnamamido)morphinan, 17-cyclopropylmethyl-4,5α-epoxy-3,14β-dihydroxy-6β-(N-methyl-3-bromocinnamamido)morphinan, 17-cyclopropylmethyl-4,5α-epoxy-3,14β-dihydroxy-6α-(N-methyl-4-bromocinnamamido)morphinan, 17-cyclopropylmethyl-4,5α-epoxy-3,14β-dihydroxy-6β-(N-methyl-4-bromocinnamamido)morphinan, 17-cyclopropylmethyl-4,5α-epoxy-3,14β-dihydroxy-6α-(N-methyl-3,4-dibromocinnamamido)morphinan, 17-cyclopropylmethyl-4,5α-epoxy-3,14β-dihydroxy-6β-(N-methyl-3,4-dibromocinnamamido)morphinan, 17-cyclopropylmethyl-4,5α-epoxy-3,14β-dihydroxy-6α-(N-methyl-3-trifluoromethylcinnamamido)morphinan, 17-cyclopropylmethyl-4,5α-epoxy-3,14β-dihydroxy-6β-(N-methyl-3-trifluoromethylcinnamamido)morphinan, 17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6β-(N-methyl-4-trifluoromethylcinnamamido)morphinan, 17-cyclopropylmethyl-4,5α-epoxy-3,14β-dihydroxy-6α-(N-methyl-3-fluoro-4-bromocinnamamido)morphinan, 17-cyclopropylmethyl-4,5α-epoxy-3,14β-dihydroxy-6β-(N-methyl-3-fluoro-4-bromocinnamamido)morphinan, 17-cyclopropylmethyl-4,5α-epoxy-3,14β-dihydroxy-6α-(N-methyl-3-bromo-4-fluorocinnamamido)morphinan, 17-cyclopropylmethyl-4,5α-epoxy-3,14β-dihydroxy-6β-(N-methyl-3-bromo-4-fluorocinnamamido)morphinan, 17-cyclopropylmethyl-4,5α-epoxy-3,14β-dihydroxy-6α-(N-methyl-3-fluoro-4-chlorocinnamamido)morphinan, 17-cyclopropylmethyl-4,5α-epoxy-3,14β-dihydroxy-6β-(N-methyl-3-fluoro-4-chlorocinnamamido)morphinan, 17-cyclopropylmethyl-4,5α-epoxy-3,14β-dihydroxy-6α-(N-methyl-3-fluoro-4-trifluoromethylcinnamamido)morphinan, 17-cyclopropylmethyl-4,5α-epoxy-3,14β-dihydroxy-6β-(N-methyl-3-fluoro-4-trifluoromethylcinnamamido)morphinan, 17-cyclopropylmethyl-4,5α-epoxy-3,14β-dihydroxy-6α-(N-methyl-3-trifluoromethyl-4-fluorocinnamamido)morphinan, 17-cyclopropylmethyl-4,5α-epoxy-3,14β-dihydroxy-6β-(N-methyl-3-trifluoromethyl-4-fluorocinnamamido)morphinan, 17-cyclopropylmethyl-4,5α-epoxy-3,14β-dihydroxy-6α-(N-methyl-3-fluoro-4-methoxycinnamamido)morphinan, 17-cyclopropylmethyl-4,5α-epoxy-3,14β-dihydroxy-6β-(N-methyl-3-fluoro-4-methoxycinnamamido)morphinan, 17-cyclopropylmethyl-4,5α-epoxy-3,14β-dihydroxy-6α-(N-methyl-3-methoxy-4-fluorocinnamamido)morphinan, 17-cyclopropylmethyl-4,5α-epoxy-3,14β-dihydroxy-6β-(N-methyl-3-methoxy-4-fluorocinnamamido)morphinan, 17-cyclopropylmethyl-4,5α-epoxy-3,14β-dihydroxy-6α-(N-methyl-3-bromo-4-methoxycinnamamido)morphinan, 17-cyclopropylmethyl-4,5α-epoxy-3,14β-dihydroxy-6β-(N-methyl-3-bromo-4-methoxycinnamamido)morphinan, 17-cyclopropylmethyl-4,5α-epoxy-3,14β-dihydroxy-6α-(N-methyl-3-methoxycinnamamido)morphinan, 17-cyclopropylmethyl-4,5α-epoxy-3,14β-dihydroxy-6β-(N-methyl-3-methoxycinnamamido)morphinan, 17-cyclopropylmethyl-4,5α-epoxy-3,14β-dihydroxy-6α-(N-methyl-4-methoxycinnamamido)morphinan, 17-cyclopropylmethyl-4,5α-epoxy-3,14β-dihydroxy-6β-(N-methyl-4-methoxycinnamamido)morphinan, 17-cyclopropylmethyl-4,5α-epoxy-3,14β-dihydroxy-6α-(N-methyl-3,4-dimethoxycinnamamido)morphinan, 17-cyclopropylmethyl-4,5α-epoxy-3,14β-dihydroxy-6β-(N-methyl-3,4-dimethoxycinnamamido)morphinan, 17-cyclopropylmethyl-4,5α-epoxy-3,14β-dihydroxy-6α-(N-methyl-3-ethoxycinnamamido)morphinan, 17-cyclopropylmethyl-4,5α-epoxy-3,14β-dihydroxy-6β-(N-methyl-3-ethoxycinnamamido)morphinan, 17-cyclopropylmethyl-4,5α-epoxy-3,14β-dihydroxy-6α-(N-methyl-3-methylcinnamamido)morphinan, 17-cyclopropylmethyl-4,5α-epoxy-3,14β-dihydroxy-6β-(N-methyl-3-methylcinnamamido)morphinan, 17-cyclopropylmethyl-4,5α-epoxy-3,14β-dihydroxy-6α-(N-methyl-4-methylcinnamamido)morphinan, 17-cyclopropylmethyl-4,5α-epoxy-3,14β-dihydroxy-6β-(N-methyl-4-methylcinnamamido)morphinan, 17-cyclopropylmethyl-4,5α-epoxy-3,14β-dihydroxy-6α-(N-methyl-3,4-dimethylcinnamamido)morphinan, 17-cyclopropylmethyl-4,5α-epoxy-3,14β-dihydroxy-6β-(N-methyl-3,4-dimethylcinnamamido)morphinan, 17-cyclopropylmethyl-4,5α-epoxy-3,14β-dihydroxy-6α-(N-methyl-3-(3-pyridyl)acrylamido)morphinan, 17-cyclopropylmethyl-4,5α-epoxy-3,14β-dihydroxy-6β-(N-methyl-3-(3-pyridyl)acrylamido)morphinan, 17-cyclopropylmethyl-4,5α-epoxy-3,14β-dihydroxy-6α-(N-methyl-3-(2-methoxypyridin-5-yl)acrylamido)morphinan, 17-cyclopropylmethyl-4,5α-epoxy-3,14β-dihydroxy-6β-(N-methyl-3-(2-methoxypyridin-5-yl)acrylamido)morphinan, 17-cyclopropylmethyl-4,5α-epoxy-3,14β-dihydroxy-6α-(N-methyl-β-methylcinnamamido)morphinan, 17-cyclopropylmethyl-4,5α-epoxy-3,14β-dihydroxy-6β-(N-methyl-β-methylcinnamamido)morphinan, 17-cyclopropylmethyl-4,5α-epoxy-3,14β-dihydroxy-6α-(N-methyl-2-nitrocinnamamido)morphinan, 17-cyclopropylmethyl-4,5α-epoxy-3,14β-dihydroxy-6β-(N-methyl-2-nitrocinnamamido)morphinan, 17-cyclopropylmethyl-4, 5α-epoxy-3,14β-dihydroxy-6α-(N-methyl-3-nitrocinnamamido)morphinan, 17-cyclopropylmethyl-4,5α-epoxy-3,14β-dihydroxy-6β-(N-methyl-3-nitrocinnamamido)morphinan, 17-cyclopropylmethyl-4,5α-epoxy-3,14β-dihydroxy-6α-(N-methyl-4-nitrocinnamamido)morphinan, 17-cyclopropylmethyl-4,5α-epoxy-3,14β-dihydroxy-6β-(N-methyl-4-nitrocinnamamido)morphinan, 17-cyclopropylmethyl-4,5α-epoxy-3,14β-dihydroxy-6α-(N-ethyl-3-trifluoromethylcinnamamido)morphinan, 17-cyclopropylmethyl-4,5α-epoxy-3,14β-dihydroxy-6β-(N-ethyl-3-trifluoromethylcinnamamido)morphinan, 17-cyclopropylmethyl-4,5α-epoxy-3,14β-dihydroxy-6α-(N-isopropyl-3-trifluoromethylcinnamamido)morphinan, 17-cyclopropylmethyl-4,5α-epoxy-3,14β-dihydroxy-6β-(N-isopropyl-3-trifluoromethylcinnamamido)morphinan, 17-cyclopropylmethyl-4,5α-epoxy-3,14β-dihydroxy-6α-(N-butyl-3-trifluoromethylcinnamamido)morphinan, 17-cyclopropylmethyl-4,5α-epoxy-3,14β-dihydroxy-6β-(N-butyl-3-trifluoromethylcinnamamido)morphinan, 17-cyclopropylmethyl-4,5α-epoxy-3,14β-dihydroxy-6α-(N-isobutyl-3-trifluoromethylcinnamamido)morphinan, 17-cyclopropylmethyl-4,5α-epoxy-3,14β-dihydroxy-6β-(N-isobutyl-3-trifluoromethylcinnamamido)morphinan, 17-cyclopropylmethyl-4,5α-epoxy-3,14β-dihydroxy-6α-(N-cyclohexylmethyl-3-trifluoromethylcinnamamido)morphinan, 17-cyclopropylmethyl-4,5α-epoxy-3,14β-dihydroxy-6β-(N-cyclohexylmethyl-3-trifluoromethylcinnamamido)morphinan, 17-cyclopropylmethyl-4,5α-epoxy-3,14β-dihydroxy-6α-(N-phenethyl-3-trifluoromethylcinnamamido)morphinan, 17-cyclopropylmethyl-4,5α-epoxy-3,14β-dihydroxy-6β-(N-phenethyl-3-trifluoromethylcinnamamido)morphinan, 17-cyclopropylmethyl-4,5α-epoxy-3,14β-dihydroxy-6α-(N-phenylpropyl-3-chlorocinnamamido)morphinan, 17-cyclopropylmethyl-4,5α-epoxy-3,14β-dihydroxy-6β-(N-phenylpropyl-3-chlorocinnamamido)morphinan, 17-cyclopropylmethyl-4,5α-epoxy-3,14β-dihydroxy-6α-(N-isobutyl-3-chlorocinnamamido)morphinan, 17-cyclopropylmethyl-4,5α-epoxy-3,14β-dihydroxy-6β-(N-isobutyl-3-chlorocinnamamido)morphinan, 17-cyclopropylmethyl-4,5α-epoxy-3,14β-dihydroxy-6α-(N-methyl-trans-3-(3-furyl)acrylamido)morphinan, 17-cyclopropylmethyl-4,5α-epoxy-3,14β-dihydroxy-6β-(N-methyl-trans-3-(3-furyl)acrylamido)morphinan, 17-cyclopropylmethyl-4,5α-epoxy-3-hydroxy-6α-(N-methyl-trans-3-(3-furyl)acrylamido)morphinan, 17-cyclopropylmethyl-4,5α-epoxy-3-hydroxy-6β-(N-methyl-trans-3-(3-furyl)acrylamido)morphinan, 17-cyclopropylmethyl-4,5α-epoxy-3-acetoxy-14β-hydroxy-6α-(N-methyl-trans-3-(3-furyacrylamido)morphinan, 17-cyclopropylmethyl-4,5α-epoxy-3-acetoxy-14β-hydroxy-6β-(N-methyl-trans-3-(3-furyl)acrylamido)morphinan, 17-cyclopropylmethyl-4,5α-epoxy-3-hydroxy-14β-acetoxy-6α-(N-methyl-trans-3-(3-furyl)acrylamido)morphinan, 17-cyclopropylmethyl-4,5α-epoxy-3-hydroxy-14β-acetoxy-6β-(N-methyl-trans-3-(3-furyl)acrylamido)morphinan, 17-cyclopropylmethyl-4,5α-epoxy-3,14β-diacetoxy-6α-(N-methyl-trans-3-(3-furyl)acrylamido)morphinan, 17-cyclopropylmethyl-4,5α-epoxy-3,14β-diacetoxy-6β-(N-methyl-trans-3-(3-furyl)acrylamido)morphinan, 17-methyl-4,5α-epoxy-3,14β-dihydroxy-6α-(N-methyl-trans-3-(3-furyl)acrylamido)morphinan, 17-methyl-4,5α-epoxy-3,14β-dihydroxy-6β-(N-methyl-trans-3-(3-furyl)acrylamido)morphinan, 17-allyl-4,5α-epoxy-3,14β-dihydroxy-6α-(N-methyl-trans-3-(3-furyl)acrylamido)morphinan, 17-allyl-4,5α-epoxy-3,14β-dihydroxy-6β-(N-methyl-trans-3-(3-furyl)acrylamido)morphinan, 17-butyl-4,5α-epoxy-3,14β-dihydroxy-6α-(N-methyl-trans-3-(3-furyl)acrylamido)morphinan, 17-butyl-4,5α-epoxy-3,14β-dihydroxy-6β-(N-methyl-trans-3-(3-furyl)acrylamido)morphinan, 17-cyclobutylmethyl-4,5α-epoxy-3,14β-dihydroxy-6α-(N-methyl-trans-3-(3-furyl)acrylamido)morphinan, 17-cyclobutylmethyl-4,5α-epoxy-3,14β-dihydroxy-6β-(N-methyl-trans-3-(3-furyl)acrylamido)morphinan, 17-isobutyl-4,5α-epoxy-3,14β-dihydroxy-6α-(N-methyl-trans-3-(3-furyl)acrylamido)morphinan, 17-isobutyl-4,5α-epoxy-3,14β-dihydroxy-6β-(N-methyl-trans-3-(3-furyl)acrylamido)morphinan, 17-phenethyl-4,5α-epoxy-3,14β-dihydroxy-6α-(N-methyl-trans-3-(3-furyl)acrylamido)morphinan, 17-phenethyl-4,5α-epoxy-3,14β-dihydroxy-6β-(N-methyl-trans-3-(3-furyl)acrylamido)morphinan, 17-cyclopropylmethyl-4,5α-epoxy-3-methoxy-14β-hydroxy-6α-(N-methyl-trans-3-(3-furyl)acrylamido)morphinan, 17-cyclopropylmethyl-4,5α-epoxy-3-methoxy-14β-hydroxy-6β-(N-methyl-trans-3-(3-furyl)acrylamido)morphinan, 17-cyclopropylmethyl-4,5α-epoxy-3,10α,14β-trihydroxy-6α-(N-methyl-trans-3-(3-furyl)acrylamido)morphinan, 17-cyclopropylmethyl-4,5α-epoxy-3,10α,14β-trihydroxy-6β-(N-methyl-trans-3-(3-furyl)acrylamido)morphinan, 17-cyclopropylmethyl-4,5α-epoxy-3,10β,14β-trihydroxy-6α-(N-methyl-trans-3-(3-furyl)acrylamido)morphinan, 17-cyclopropylmethyl-4,5α-epoxy-3,10β,14β-trihydroxy-6β-(N-methyl-trans-3-(3-furyl)acrylamido)morphinan, 17-cyclopropylmethyl-4,5α-epoxy-3,14β-dihydroxy-10-oxo-6α-(N-methyl-trans-3-(3-furyl)acrylamido)morphinan, 17-cyclopropylmethyl-4,5α-epoxy-3,14β-dihydroxy-10-oxo-6β-(N-methyl-trans-3-(3-furyl)acrylamido)morphinan, 17-cyclopropylmethyl-4,5α-epoxy-3,14β-dihydroxy-6α-(N-methyl-trans-3-(2-furyl)acrylamido)morphinan, 17-cyclopropylmethyl-4,5α-epoxy-3,14β-dihydroxy-6β-(N-methyl-trans-3-(2-furyl)acrylamido)morphinan, 17-cyclopropylmethyl-4,5α-epoxy-3,14β-dihydroxy-6α-(N-methyl-trans-3-(thiophen-3-yl)acrylamido)morphinan, 17-cyclopropylmethyl-4,5α-epoxy-3,14β-dihydroxy-6β-(N-methyl-trans-3-(thiophen-3-yl)acrylamido)morphinan, 17-cyclopropylmethyl-4,5α-epoxy-3,14β-dihydroxy-6α-(N-methyl-trans-3-(thiophen-2-yl)acrylamido)morphinan, 17-cyclopropylmethyl-4,5α-epoxy-3,14β-dihydroxy-6β-(N-methyl-trans-3-(thiophen-2-yl)acrylamido)morphinan, 17-cyclopropylmethyl-4,5α-epoxy-3,14β-dihydroxy-6α-(N-methyl-trans-3-(2-(3-bromothiophen-2-yl)acrylamido)morphinan, 17-cyclopropylmethyl-4,5α-epoxy-3,14β-dihydroxy-6β-(N-methyl-trans-3-(2-(3-bromothiophen-2-yl)acrylamido)morphinan, 17-cyclopropylmethyl-4,5α-epoxy-3,14β-dihydroxy-6α-(N-methylphenylpropanoylamido)morphinan, 17-cyclopropylmethyl-4,5α-dihydroxy-6β-(N-methylphenylpropanoylamido)morphinan, 17-cyclopropylmethyl-4,5α-dihydroxy-6α-(N-methylphenylbutanoylamido)morphinan, 17-cyclopropylmethyl-4,5α-dihydroxy-6β-(N-methylphenylbutanoylamido)morphinan, 17-cyclopropylmethyl-4,5α-dihydroxy-6α-(N-methylphenylpentanoylamido)morphinan, 17-cyclopropylmethyl-4,5α-dihydroxy-6β-(N-methylphenylpentanoylamido)morphinan, 17-cyclopropylmethyl-4,5α-dihydroxy-6α-(N-methylphenylhexanoylamido)morphinan, 17-cyclopropylmethyl-4,5α-epoxy-3,14β- dihydroxy-6β-(N-methylphenylhexanoylamido)morphinan, 17-cyclopropylmethyl-4,5α-epoxy-3,14β-dihydroxy-6α-(N-methylacetamido)morphinan, 17-cyclopropylmethyl-4,5α-epoxy-3,14β-dihydroxy-6β-(N-methylacetamido)morphinan, 17-cyclopropylmethyl-4,5α-epoxy-3,14β-dihydroxy-6α-(N-methylpropanoylamido)morphinan, 17-cyclopropylmethyl-4,5α-epoxy-3,14β-dihydroxy-6β-(N-methylpropanoylamido)morphinan, 17-cyclopropylmethyl-4,5α-epoxy-3,14β-dihydroxy-6α-(N-methylbutanoylamido)morphinan, 17-cyclopropylmethyl-4,5α-epoxy-3,14β-dihydroxy-6β-(N-methylbutanoylamido)morphinan, 17-cyclopropylmethyl-4,5α-epoxy-3,14β-dihydroxy-6α-(N-methylpentanoylamido)morphinan, 17-cyclopropylmethyl-4,5α-epoxy-3,14β-dihydroxy-6β-(N-methylpentanoylamido)morphinan, 17-cyclopropylmethyl-4,5α-epoxy-3,14β-dihydroxy-6α-(N-methylhexanoylamido)morphinan, 17-cyclopropylmethyl-4,5α-epoxy-3,14β-dihydroxy-6β-(N-methylhexanoylamido)morphinan, 17-cyclopropylmethyl-4,5α-epoxy-3,14β-dihydroxy-6α-(N-methyl-2-hexenoylamido)morphinan, 17-cyclopropylmethyl-4,5α-epoxy-3,14β-dihydroxy-6β-(N-methyl-2-hexenoylamido)morphinan, 17-cyclopropylmethyl-4,5α-epoxy-3,14β-dihydroxy-6α-(N-methyl-2,4-hexadienoylamido)morphinan, 17-cyclopropylmethyl-4,5α-epoxy-3,14β-dihydroxy-6β-(N-methyl-2,4-hexadienoylamido)morphinan, 17-cyclopropylmethyl-4,5α-epoxy-3,14β-dihydroxy-6α-(N-methyl-5-methyl-2-hexenoylamido)morphinan, 17-cyclopropylmethyl-4,5α-epoxy-3,14β-dihydroxy-6β-(N-methyl-5-methyl-2-hexenoylamido)morphinan, 17-cyclopropylmethyl-4,5α-epoxy-3,14β-dihydroxy-6α-(N-methyl-4-methyl-2-hexenoylamido)morphinan, 17-cyclopropylmethyl-4,5α-epoxy-3,14β-dihydroxy-6β-(N-methyl-4-methyl-2-hexenoylamido)morphinan, 17-cyclopropylmethyl-4,5α-epoxy-3,14β-dihydroxy-6α-(N-methyl-3-cyclohexylpropanoylamido)morphinan, 17-cyclopropylmethyl-4,5α-epoxy-3,14β-dihydroxy-6β-(N-methyl-3-cyclohexylpropanoylamido)morphinan, 17-cyclopropylmethyl-4,5α-epoxy-3,14β-dihydroxy-6α-(N-methyl-3-cyclohexyl-2-propenoylamido)morphinan, 17-cyclopropylmethyl-4,5α-epoxy-3,14β-dihydroxy-6β-(N-methyl-3-cyclohexyl-2-propenoylamido)morphinan, 17-cyclopropylmethyl-4,5α-epoxy-3,14β-dihydroxy-6α-(N-methyl-N'-benzylcarbamoyl)morphinan, 17-cyclopropylmethyl-4,5α-epoxy-3,14β-dihydroxy-6β-(N-methyl-N'-benzylcarbamoyl)morphinan, 17-cyclopropylmethyl-4,5α-epoxy-3,14β-dihydroxy-6α-(N-methylphenoxyacetamido)morphinan, 17-cyclopropylmethyl-4,5α-epoxy-3,14β-dihydroxy-6β-(N-methylphenoxyacetamido)morphinan, 17-cyclopropylmethyl-4,5α-epoxy-3,14β-dihydroxy-6α-(N-methylthiophenoxyacetamido)morphinan, 17-cyclopropylmethyl-4,5α-epoxy-3,14β-dihydroxy-6β-(N-methylthiophenoxyacetamido)morphinan, 17-cyclopropylmethyl-4,5α-epoxy-3,14β-dihydroxy-6α-(N-methyl-N'-phenylaminoacetamido)morphinan, 17-cyclopropylmethyl-4,5α-epoxy-3,14β-dihydroxy-6β-(N-methyl-N'-phenylaminoacetamido)morphinan The compounds per se represented by the above-described Formula (I) are known, and can be produced by known methods. For example, among the compounds represented by Formula (I), those wherein both $R^{12}$ and $R^{13}$ are hydrogen can be produced by the method described in Japanese Patent No. 2525552. Among the compounds represented by Formula (I), those wherein $R^{12}$ and $R^{13}$ together form oxo can be produced by, for example, the method described in Chem. Pharm. Bull. 52, 664 (2004) and in Japanese Patent No. 2525552, using the compounds having a 10-oxo group, which are obtained by the method described in a reference (Heterocycles, 63, 865 (2004), Bioorg. Med. Chem. Lett., 5, 1505 (1995)) as a starting material. Further, among the compounds represented by Formula (1), those wherein $R^{12}$ is hydrogen and $R^{13}$ is hydroxy, and those wherein $R^{12}$ is hydroxy and $R^{13}$ is hydrogen can be produced by the method described in Chem. Pharm. Bull. 52, 664 (2004).

Preferred examples of the pharmaceutically acceptable acid addition salts of the above-described compounds include, but not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are especially preferred.

These compounds are purified such that they can be applied to medical use. After passing the requisite safety tests, they can be administered orally or parenterally as they are, or as a pharmaceutical composition after being admixed with a known pharmaceutically acceptable acid(s), carrier(s), vehicle(s) and/or the like. For oral administration, formulations such as tablets, capsules, powders, granules and the like can be selected; and for parenteral administration, intravenous rapid infusion, intravenous sustained infusion, intramuscular injection, intradermal injection, subcutaneous injection and the like can be selected, although the administration routes are not limited thereto.

The content of the compound in the pharmaceutical composition is not restricted, and the pharmaceutical composition is usually formulated such that a dosage range of 0.1 µg to 100 mg per once is attained for both oral and parenteral administration. The dose can be selected appropriately depending on the symptom of the patient, and the like, and is usually about 0.1 µg to 20 mg, preferably about 1 µg to 10 mg per day per adult as amount of an active ingredient which is compound represented by Formula (I).

The compound of the present invention can also be used in combination with a drug(s) used for the prophylaxis or therapy of multiple sclerosis. Examples of the drugs for prophylaxis or therapy of multiple sclerosis include adrenocorticosteroids for the purpose of acute stage therapy, such as cortisone acetate, hydrocortisone, phosphoric acid hydrocortisone, hydrocortisone succinate, prednisolone, prednisolone succinate, methylprednisolone, methylprednisolone acetate, methylprednisolone succinate, triamcinolone, triamcinolone diacetate, dexamethasone, dexamethasone phosphate, dexamethasone palmitate, betamethasone, betamethasone phosphate, paramethasone acetate, fludrocortisone acetate and halopredone acetate; interferons for the purpose of inhibition of recurrence or progress, such as interferon-beta and interferon beta-1b (genetic recombination); immunosuppressive agents such as azathioprine, mizoribine, mycophenolate mofetil, methotrexate, leflunomide, cyclophosphamide, cyclosporin, neoral, tacrolimus hydrate, gusperimus hydrochloride, muromonab-CD3 and basiliximab; muscle relaxants for the purpose of treatment of ataxia, such as tolperisone hydrochloride, methocarbamol, phenprobamate, pridinol mesilate, chlorphenesin carbamate, baclofen, piracetam, eperisone hydrochloride, afloqualone, tizanidine hydrochloride, hydrochloric acid suxamethonium, dantrolene sodium, pancuronium bromide and vecuronium bromide; antiepileptics for the purpose of therapy of sensory impairment, such as primidone, phenyloin, ethotoin, trimethadione, sultiame, ethosuximide, acetylpheneturide, clonazepam, diazepam, clobazam, carbamazepine, sodium valproate and zonisamide; tricyclic antidepressants such as imipramine hydrochloride, clomipramine hydrochloride, trimipramine maleate, amitriptyline hydrochloride, nortriptyline hydrochloride, lofepramine hydrochloride, amoxapine, dosulepin hydrochloride; anticholinesterases for the purpose of treatment of dysuria, such as ambenonium chloride, edrophonium chloride and distigmine bromide; therapeutic agents for frequent urination and the like, such as flavoxate hydrochloride, oxybutynin hydrochloride, propiverine hydrochloride and mesna; psychostimulants for the purpose of fatigue improvements, such as pemoline and dopamine releaser such as amantadine hydrochloride.

In the present invention, MRL/lpr mice which spontaneously increase scratching behavior accompanying IgG production with aging under SPF (Specific Pathogen Free: which means that specific microorganisms or parasites do not exist) conditions in which influence by the factors which can be external factors such as allergens is small. As an animal experimental system of multiple sclerosis, experimental autoimmune encephalomyelitis (EAE) induced by immunization with myelin basic protein which is a component of central nervous system has been reported (J. Neuroimmunol. 38(3), 229-240 (1992)). However, although this experimental system has inflammatory and immunological homologies to multiple sclerosis, it does not induce pruritus which is a symptom caused by multiple sclerosis. Therefore, it was difficult to evaluate antipruritic effect against the pruritus caused by multiple sclerosis. In view of this, the present inventors focused attention on MRL/lpr mouse. This strain is an animal model widely used as a model of autoimmune diseases, and inflammation of central nervous tissue or neurogenic abnormal behavior thereof has been reported (Scand. J. Rheumatol. 12, 263-273 (1995)). As a result of careful examination of the MRL/lpr mouse, it was confirmed that the mouse scratches in response to pruritus as described in Reference Example 1 below. Further, the fact that both the number of scratching and the serum IgG level which is an index indicating the degree of activation of immune system were larger in female recalled the fact that multiple sclerosis occurs more frequently in female. Thus, MRL/lpr mouse is the model which best reflects the pruritus of multiple sclerosis among the existing evaluation systems, and the present inventors discovered that a compound which is effective in this evaluation system can be an antipruritic against the pruritus caused by multiple sclerosis.

The present invention will now be described more concretely by way of examples.

EXAMPLES

Reference Example 1

Change in Number of Scratching Behavior and Serum Anti-Immunoglobulin Titer with Age in Week in MRL/Lpr Mice Female and male MRL/Ipr mice kept under SPF conditions were placed in a cage for observation (one compartment: 10 cm*14 cm*30 cm) such that one mouse was placed in one compartment. Thereafter, the behavior of each mouse was recorded with an unattended video camera above the mice for one hour, thereby studying the change in the number spontaneous scratching behavior with aging. The recording was carried out on the same mouse from 8 weeks old to 20 weeks old at a frequency of once per 2 weeks. The scratching behavior was observed by replaying the video tape, and the number of scratching behavior with a hind leg was counted visually. The number of scratching behavior was counted such that the series of behavior from raising the hind leg for starting the scratching to putting down the hind leg were counted as one scratching behavior. The results are shown in Table 1. It was proved that the mean number of scratching behavior in an hour of the female mice of not younger than 10 weeks old exceeded 40 times. In the table, the symbol "**" indicates that the result is statistically significant (p<0.01) with respect to the control group (at the time of 8 weeks old) (multiple comparison between time points in one group). When compared with male mice, female MRL/lpr mice showed prominent scratching behavior from 10 weeks old, and the mean number of scratching behavior at 20 weeks old exceeded 300 times. Thus, it was shown that it is desired to use female mice for evaluation.

Further, the change in serum immunoglobulin antibody level (IgG and IgE antibody levels) with aging was studied. The samples were collected from the same mouse by collection of blood from eyeground, from 8 weeks old to 20 weeks old at a frequency of once per 2 weeks, and the antibody levels were determined by EIA. The results are shown in FIG. 1. The serum IgG antibody level raised with aging and female mice showed more prominent increase than male mice. The IgG antibody level of female mice reached plateau at 14 weeks old, and was about 12 mg/mL on average. Thus, raise of IgG antibody level which is a character of multiple sclerosis was confirmed. From these, it was shown that raise in IgG level correlated with the number of scratching behavior. As for the blood IgE antibody level, although a transient slight increase was observed in female mice, it was not prominent and the antibody level was not more than 2 μg/mL on average. These results indicate that they have a similar character to that of multiple sclerosis wherein the prominent raise of IgE antibody level is not observed.

TABLE 1

Change in Scratching Behavior with Age in Week in MRL/lpr Mice

| Age in Week | Number of Scratching Behavior (60 minutes) Mean ± S.E. | | | |
|---|---|---|---|---|
| weeks old | Female | | Male | |
| 8 | 18.5 ± 4.2 | — | 25.1 ± 5.9 | — |
| 10 | 57.6 ± 3.3 | ** | 25.9 ± 4.2 | — |
| 12 | 66.0 ± 7.2 | ** | 28.6 ± 5.7 | — |
| 14 | 49.6 ± 6.2 | ** | 50.5 ± 9.1 | ** |
| 16 | 110.9 ± 41.5 | ** | 34.5 ± 7.4 | — |
| 18 | 213.1 ± 47.9 | ** | 41.2 ± 11.2 | ** |
| 20 | 347.8 ± 76.8 | ** | 77.3 ± 16.5 | ** |

** p<0.01 (multiple comparison between time points in one group, vs. number of scratching behavior of female or male mice at 8 weeks old)

Example

Effect of (−)-17-cyclopropylmethyl-4,5α-epoxy-3, 14β-dihydroxy-6β-(N-methyl-trans-3-(3-furyl)acrylamido)morphinan hydrochloric acid salt (Compound 1) on Spontaneous Scratching Behavior in MRL/lpr Mice Using 20 weeks old female MRL/lpr mice which showed spontaneous scratching behavior, the inhibitory effect, that is, antipruritic effect of Compound 1

Compound 1

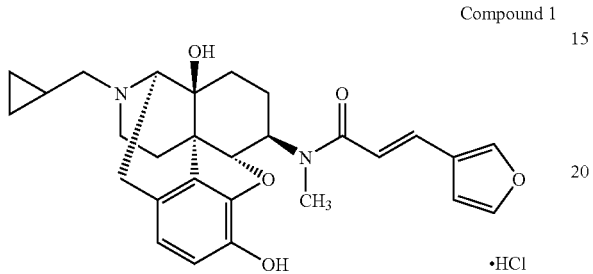

which is an κ opioid receptor agonist compound against pruritus was evaluated. The evaluation was carried out over 5 days dividedly. On Day 1, sterilized distilled water was orally administered 30 minutes before the beginning of the recording of the scratching behavior, and the number of scratching behavior when the mouse received a solvent was counted for 60 minutes. On Day 2, Compound 1 was orally administered to the same mouse 30 minutes before the beginning of the recording of the scratching behavior at a dose of 3 μg/kg, and the number of scratching behavior was counted for 60 minutes. On Days 3 to 5, the experiments were carried out in the same schedule as in Day 2 increasing the dose of Compound 1 such that the doses of Compound 1 on Day 3, Day 4 and Day 5 were 10 μg/kg, 30 μg/kg and 100 μg/kg, respectively (n=8). The recording was carried out under SPF conditions by placing the mice in a cage for observation (one compartment: 10 cm*14 cm*30 cm) such that one mouse was placed in one compartment, then recording the behavior of each mouse with an unattended video camera above the mice for one hour. The number of scratching behavior was counted visually by replaying the video tape. The number of scratching behavior was counted such that the series of behavior from raising the hind leg for starting the scratching to putting down the hind leg were counted as one scratching behavior.

As a control compound, chlorophenylamine which is an antihistaminic agent was used. Chlorophenylamine was orally administered to the same mouse 60 minutes before the beginning of the measurement of the scratching behavior increasing the dose such that the dose was 0 mg/kg (solvent alone was administered) on Day 1, 3 mg/kg on Day 2, 10 mg/kg on Day 3 and 30 mg/kg on Day 4 (n=8). The counting of the scratching behavior was carried out in the same manner that for Compound 1.

Figures 1, 2:
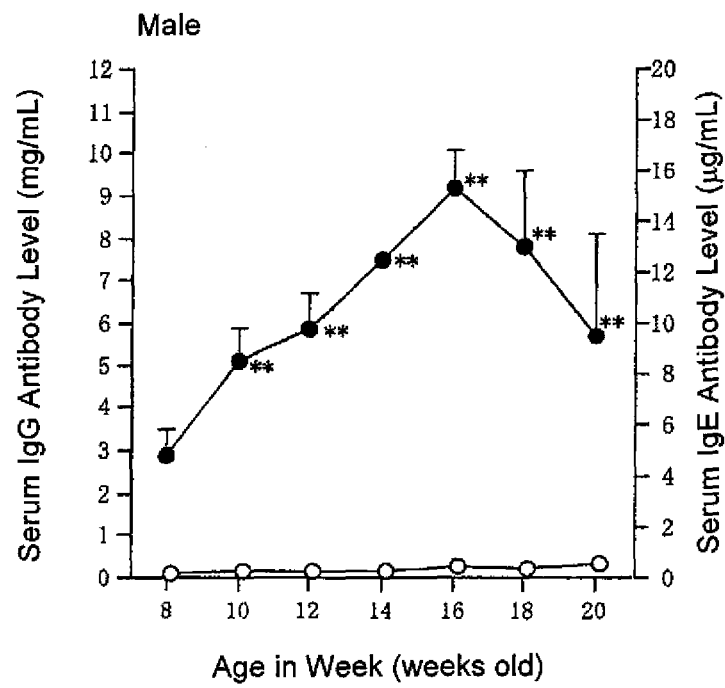
Figure 2:
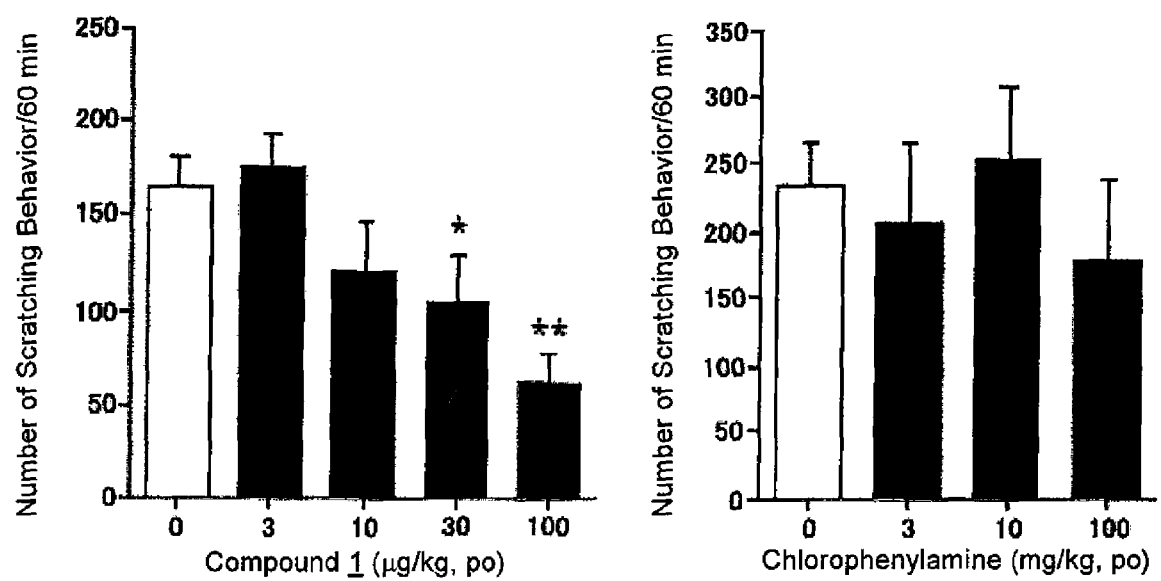

Statistical analysis was carried out by multiple comparison between time points in one group employing the time point at which the solvent alone was administered as a control group. The results of the studies described above are shown in FIG. 2. The numbers of scratching behavior of the mice to which Compound 1 was orally administered in an amount of 30 μg/kg and 100 μg/kg, respectively, decreased when compared with that of the control group at the time of administration of the solvent, and the differences from that of the control group were statistically significant at statistical levels of 5% and 1%, respectively. On the other hand, chlorophenylamine which is an antihistaminic agent did not show inhibitory effect at any does. Thus, it was shown that Compound 1 is effective against the pruritus of multiple sclerosis, which is resistant to the existing drugs.

The invention claimed is:

1. A method for reducing pruritus caused by multiple sclerosis, said method comprising the steps of:
    identifying a patient having pruritus caused by multiple sclerosis; and
    administering an effective amount of a compound represented by Formula (I) to said patient

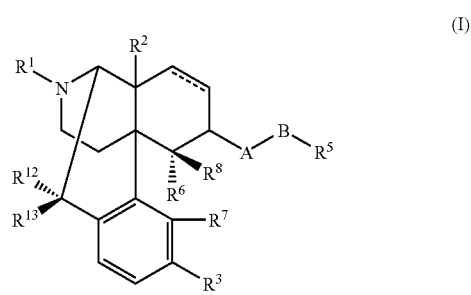

(I)

wherein
  $\vdots$ represents a double bond or single bond;
  $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (wherein the number of carbon atoms in the alkyl moiety is 1 to 5) or thiophen-2-ylalkyl (wherein the number of carbon atoms in the alkyl moiety is 1 to 5);
  $R^2$ represents hydrogen, hydroxy, nitro, $C_1$-$C_5$ alkanoyloxy, $C_1$-$C_5$ alkoxy, $C_1$-$C_5$ alkyl or $NR^9R^{10}$ wherein $R^9$ represents hydrogen or $C_1$-$C_5$ alkyl and $R^{10}$ represents hydrogen or $C_1$-$C_5$ alkyl or —C(=O)$R^{11}$ wherein $R^{11}$ represents hydrogen, phenyl or $C_1$-$C_5$ alkyl;
  $R^3$ represents hydrogen, hydroxy, $C_1$-$C_5$ alkanoyloxy or $C_1$-$C_5$ alkoxy;
  A represents —XC(=Y)—, —XC(=Y)Z—, —X— or —XSO$_2$— (wherein X, Y and Z independently represent $NR^4$, S or O wherein $R^4$ represents hydrogen, $C_1$-$C_5$ linear or branched alkyl or $C_6$-$C_{12}$ aryl, and wherein $R^4$s in the formula may be the same or different);
  B represents valence bond, $C_1$-$C_{14}$ linear or branched alkylene (wherein said alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), $C_2$-$C_{14}$ linear or branched acyclic unsaturated hydrocarbon containing 1 to 3 double bonds and/or triple bonds (wherein said acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), or $C_1$-$C_{14}$ linear or branched saturated or unsaturated hydrocarbon containing 1 to 5 thioether bonds, ether bonds and/or amino bonds (with the proviso that a hetero atom does not directly binds to A, and wherein 1 to 3 methylene groups therein may be replaced by a carbonyl group(s));

R⁵ represents hydrogen or an organic group having a skeleton selected from those shown below

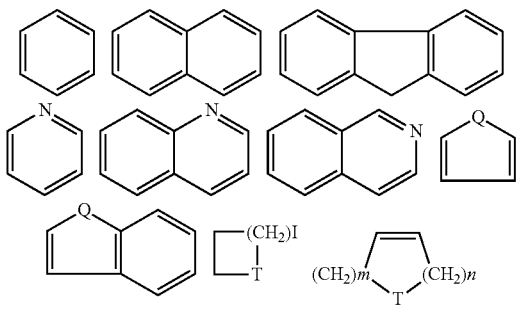

wherein Q represents NH, O, or S; T represents CH₂, NH, S, or O; l represents an integer of 0 to 5; and m and n independently represent integers of 0 to 5, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy;

R⁶ represents hydrogen: R⁷ represents hydrogen, hydroxy, $C_1$-$C_5$ alkoxy or $C_1$-$C_5$ alkanoyloxy; or R⁶ and R⁷ together represent —O—, —CH₂— or —S—;

R⁸ represents hydrogen, $C_1$-$C_5$ alkyl or $C_1$-$C_5$ alkanoyl; and

R¹² and R¹³ both represent hydrogen, or one of them represents hydrogen and the other represents hydroxy, or they together represent oxo; and the Formula (I) includes (+), (−) and (±) isomers or a pharmaceutically acceptable acid addition salt thereof.

2. The method according to claim 1, comprising as the effective ingredient a compound represented by the Formula (I) wherein R¹ is methyl, ethyl, propyl, butyl, isobutyl, cyclopropylmethyl, allyl, benzyl or phenethyl; R² and R³ independently are hydrogen, hydroxy, acetoxy or methoxy; A is —XC(═Y)— (wherein X represents NR⁴, S or O, Y represents O, wherein R⁴ represents hydrogen or $C_1$-$C_5$ linear or branched alkyl), —XC(═Y)Z—, —X— or —XSO₂— (wherein X represents NR⁴, Y represents O or S, and Z represents NR⁴ or O, wherein R⁴ represents hydrogen or $C_1$-$C_5$ linear or branched alkyl); B is $C_1$-$C_3$ linear alkylene; R⁶ and R⁷ together form —O—; and R⁸ is hydrogen; or a pharmaceutically acceptable acid addition salt thereof.

3. The method according to claim 2, comprising as the effective ingredient a compound represented by the Formula (I) wherein A is —XC(═Y)— or —XC(═Y)Z— (wherein X represents NR⁴; Y represents O, and Z represents O, wherein R⁴ represents $C_1$-$C_5$ linear or branched alkyl); or a pharmaceutically acceptable acid addition salt thereof.

4. The method according to claim 3, comprising as the effective ingredient a compound represented by the Formula (I) wherein R⁵ is hydrogen or an organic group having a skeleton selected from those shown below

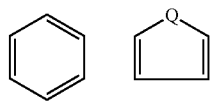

wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy; or a pharmaceutically acceptable acid addition salt thereof.

5. The method according to claim 4, comprising as the effective ingredient a compound represented by the Formula (I) wherein A is —XC(═Y)— or —XC(═Y)Z— (wherein X represents NR⁴, Y represents O, and Z represents O, wherein R⁴ represents $C_1$-$C_5$ linear or branched alkyl); or a pharmaceutically acceptable acid addition salt thereof.

6. The method according to claim 1, comprising as the effective ingredient a compound represented by the Formula (I) wherein R¹ is methyl, ethyl, propyl, butyl, isobutyl, cyclopropylmethyl, allyl, benzyl or phenethyl; R² and R³ independently are hydrogen, hydroxy, acetoxy or methoxy; A is —XC(═Y)— (wherein X represents NR⁴, and Y represents O, wherein R⁴ represents $C_1$-$C_5$ linear or branched alkyl); B is —CH═CH—, —C≡C—, —CH₂O— or —CH₂S—; R⁶ and R⁷ together form —O—; and R⁸ is hydrogen; or a pharmaceutically acceptable acid addition salt thereof.

7. The method according to claim 6, comprising as the effective ingredient a compound represented by the Formula (I) wherein R⁵ is hydrogen or an organic group having a skeleton selected from those shown below

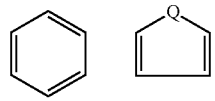

wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy; or a pharmaceutically acceptable acid addition salt thereof.

8. The method, according to claim 6, comprising as the effective ingredient a compound represented by the Formula (I) wherein B is —CH═CH— or —C≡C—, or a pharmaceutically acceptable acid addition salt thereof.

9. The method according to claim 8, comprising as the effective ingredient a compound represented by the Formula (I) wherein R⁵ is hydrogen or an organic group having a skeleton selected from those shown below

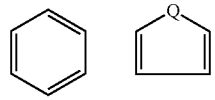

wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy; or a pharmaceutically acceptable acid addition salt thereof.

10. The method according to claim 1, wherein said compound is a compound of the formula

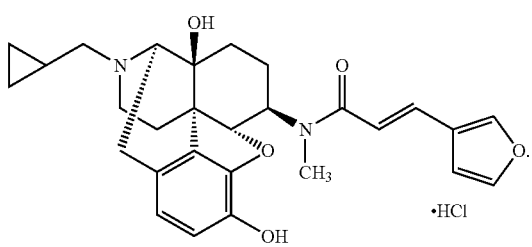 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5 ; Cl]

11. A method for reducing pruritus caused by multiple sclerosis, said method comprising the steps of:
  identifying a patient having pruritus caused by multiple sclerosis; and
  administering to said patient a drug for prophylaxis or therapy of multiple sclerosis in combination with an effective amount of a compound represented by Formula (I):

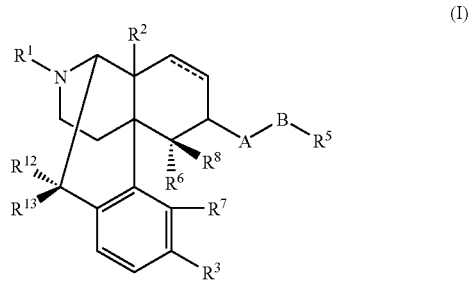

(I)

wherein
  ··· represents a double bond or single bond;
  $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (wherein the number of carbon atoms in the alkyl moiety is 1 to 5) or thiophen-2-ylalkyl (wherein the number of carbon atoms in the alkyl moiety is 1 to 5);
  $R^2$ represents hydrogen, hydroxy, nitro, $C_1$-$C_5$ alkanoyloxy, $C_1$-$C_5$ alkoxy, $C_1$-$C_5$ alkyl or $NR^9R^{10}$ wherein $R^9$ represents hydrogen or $C_1$-$C_5$ alkyl and $R^{10}$ represents hydrogen or $C_1$-$C_5$ alkyl or —C(=O)$R^{11}$ wherein $R^{11}$ represents hydrogen, phenyl or $C_1$-$C_5$ alkyl;
  $R^3$ represents hydrogen, hydroxy, $C_1$-$C_5$ alkanoyloxy or $C_1$-$C_5$ alkoxy;
  A represents —XC(=Y)—, —XC(=Y)Z—, —X— or —XSO$_2$— (wherein X, Y and Z independently represent NR$^4$, S or O wherein $R^4$ represents hydrogen, $C_1$-$C_5$ linear or branched alkyl or $C_6$-$C_{12}$ aryl, and wherein $R^4$s in the formula may be the same or different);
  B represents valence bond, $C_1$-$C_{14}$ linear or branched alkylene (wherein said alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), $C_2$-$C_{14}$ linear or branched acyclic unsaturated hydrocarbon containing 1 to 3 double bonds and/or triple bonds (wherein said acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups therein may be replaced by a carbonyl group(s)), or $C_1$-$C_{14}$ linear or branched saturated or unsaturated hydrocarbon containing 1 to 5 thioether bonds, ether bonds and/or amino bonds (with the proviso that a hetero atom does not directly binds to A, and wherein 1 to 3 methylene groups therein may be replaced by a carbonyl group(s));
  $R^5$ represents hydrogen or an organic group having a skeleton selected from those shown below

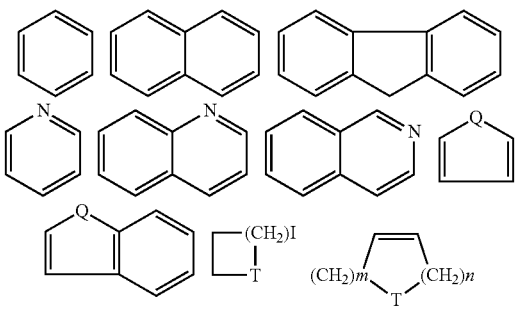

wherein Q represents NH, O, or S; T represents CH$_2$, NH, S, or O; l represents an integer of 0 to 5; and m and n independently represent integers of 0 to 5, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy;
  $R^6$ represents hydrogen: $R^7$ represents hydrogen, hydroxy, $C_1$-$C_5$ alkoxy or $C_1$-$C_5$ alkanoyloxy; or $R^6$ and $R^7$ together represent —O—, —CH$_2$— or —S—;
  $R^8$ represents hydrogen, $C_1$-$C_5$ alkyl or $C_1$-$C_5$ alkanoyl; and
  $R^{12}$ and $R^{13}$ both represent hydrogen, or one of them represents hydrogen and the other represents hydroxy, or they together represent oxo; and
  the Formula (I) includes (+), (−) and (±) isomers
or a pharmaceutically acceptable acid addition salt thereof.

* * * * *